US007459127B2

(12) United States Patent
Pugia et al.

(10) Patent No.: US 7,459,127 B2
(45) Date of Patent: Dec. 2, 2008

(54) METHOD AND APPARATUS FOR PRECISE TRANSFER AND MANIPULATION OF FLUIDS BY CENTRIFUGAL AND/OR CAPILLARY FORCES

(75) Inventors: Michael J. Pugia, Granger, IN (US); Gert Blankenstein, Dortmund (DE); Ralf-Peter Peters, Bergisch Gladbach (DE); Holger Bartos, Dortmund (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 111 days.

(21) Appl. No.: 10/082,415

(22) Filed: Feb. 26, 2002

(65) Prior Publication Data

US 2003/0166265 A1 Sep. 4, 2003

(51) Int. Cl.
*G01N 33/00* (2006.01)

(52) U.S. Cl. ........................ 422/100; 422/68.1; 422/72; 422/99; 422/81

(58) Field of Classification Search .................. 42/68.1, 42/72, 81, 99, 100
See application file for complete search history.

(56) References Cited

U.S. PATENT DOCUMENTS

| | | | | |
|---|---|---|---|---|
| 3,798,459 | A | 3/1974 | Anderson et al. | 250/218 |
| 3,799,742 | A | 3/1974 | Coleman | 23/253 R |
| 3,804,533 | A | 4/1974 | Scott | 356/197 |
| 3,856,649 | A | 12/1974 | Genshaw et al. | 204/195 |
| 3,992,158 | A | 11/1976 | Przybylowicz et al. | 23/253 TP |
| 4,233,029 | A | 11/1980 | Columbus | 23/230 R |
| 4,310,399 | A | 1/1982 | Columbus | 204/195 R |
| 4,413,407 | A | 11/1983 | Columbus | 29/825 |
| 4,446,232 | A | 5/1984 | Liotta | 435/7 |
| 4,515,889 | A | 5/1985 | Klose et al. | 435/4 |
| 4,587,220 | A | 5/1986 | Mayambala-Mwanika et al. | 436/66 |
| 4,600,507 | A | 7/1986 | Shimizu et al. | 210/94 |
| 4,618,476 | A | 10/1986 | Columbus | 422/100 |
| 4,647,654 | A | 3/1987 | Knowles et al. | 530/326 |
| 4,658,022 | A | 4/1987 | Knowles et al. | 530/402 |
| 4,676,274 | A | 6/1987 | Brown | |
| 4,727,036 | A | 2/1988 | Knowles et al. | 436/547 |
| 4,755,472 | A | 7/1988 | Ismail et al. | 436/66 |
| 4,761,381 | A | 8/1988 | Blatt et al. | 436/165 |
| 4,806,311 | A | 2/1989 | Greenquist | 422/56 |
| 4,908,112 | A | 3/1990 | Pace | 204/299 |
| 4,963,498 | A | 10/1990 | Hillman et al. | 436/69 |
| 4,968,742 | A | 11/1990 | Hillman et al. | 436/69 |
| 4,970,171 | A | 11/1990 | Messenger et al. | 436/66 |
| 5,024,647 | A | 6/1991 | Jubin et al. | 494/37 |
| 5,053,197 | A | 10/1991 | Bowen | 422/58 |
| 5,089,420 | A | 2/1992 | Albarella et al. | 436/66 |
| 5,096,836 | A | 3/1992 | Macho et al. | 436/169 |

(Continued)

FOREIGN PATENT DOCUMENTS

| | | |
|---|---|---|
| CA | 2323424 | 3/2005 |

(Continued)

*Primary Examiner*—Sam P Siefke
(74) *Attorney, Agent, or Firm*—Harold N. Wells; Noam R. Pollack

(57) ABSTRACT

A micro-liter liquid sample, particularly a biological sample, is analyzed in a device employing centrifugal and capillary forces. The sample is moved through one or more sample wells arrayed within a small flat chip via interconnecting capillary passageways. The passageways may be either hydrophobic or hydrophilic and may include hydrophobic or hydrophilic capillary stops.

26 Claims, 9 Drawing Sheets

U.S. PATENT DOCUMENTS

| | | | | | |
|---|---|---|---|---|---|
| 5,110,555 | A | | 5/1992 | Moore et al. | 422/100 |
| 5,141,868 | A | | 8/1992 | Shanks et al. | 435/288 |
| 5,151,369 | A | | 9/1992 | Lewis et al. | 436/67 |
| 5,160,702 | A | | 11/1992 | Kopf-Sill et al. | 422/72 |
| 5,164,598 | A | | 11/1992 | Hillman et al. | 250/341 |
| 5,180,480 | A | | 1/1993 | Manz | 204/299 R |
| 5,187,104 | A | | 2/1993 | Corey et al. | 436/86 |
| 5,202,261 | A | | 4/1993 | Musho et al. | 435/88 |
| 5,208,163 | A | | 5/1993 | Charlton et al. | 436/63 |
| 5,230,866 | A | * | 7/1993 | Shartle et al. | 422/103 |
| 5,250,439 | A | | 10/1993 | Musho et al. | 435/25 |
| 5,258,311 | A | | 11/1993 | Lewis et al. | 436/63 |
| 5,279,790 | A | | 1/1994 | Corey et al. | 422/55 |
| 5,286,454 | A | | 2/1994 | Nilsson et al. | 422/102 |
| 5,296,192 | A | | 3/1994 | Carroll et al. | 422/56 |
| 5,318,894 | A | | 6/1994 | Pugia | 435/28 |
| 5,360,595 | A | | 11/1994 | Bell et al. | 422/56 |
| 5,372,918 | A | | 12/1994 | Usui et al. | 430/379 |
| 5,424,125 | A | | 6/1995 | Ballard et al. | 428/364 |
| 5,443,890 | A | | 8/1995 | Öhman | 428/167 |
| 5,458,852 | A | | 10/1995 | Buechler | 422/58 |
| 5,478,751 | A | | 12/1995 | Oosta et al. | 436/165 |
| 5,585,069 | A | | 12/1996 | Zanzucchi et al. | 422/100 |
| 5,631,303 | A | | 5/1997 | Reinecke | 521/40.5 |
| 5,716,741 | A | | 2/1998 | Reinecke et al. | 430/8 |
| 5,716,851 | A | | 2/1998 | Pugia et al. | 436/86 |
| 5,826,981 | A | | 10/1998 | Fowler et al. | 366/337 |
| 5,834,314 | A | | 11/1998 | Gates et al. | |
| 5,837,200 | A | | 11/1998 | Diessel et al. | 422/73 |
| 5,851,776 | A | | 12/1998 | Valkirs | 435/7.1 |
| 5,866,345 | A | | 2/1999 | Wilding et al. | 435/7.21 |
| 5,885,527 | A | | 3/1999 | Buechler | 422/58 |
| 5,912,134 | A | | 6/1999 | Shartle | 435/7.24 |
| 5,922,615 | A | | 7/1999 | Nowakowski et al. | 436/518 |
| 5,932,315 | A | | 8/1999 | Lum et al. | 428/172 |
| 5,939,272 | A | | 8/1999 | Buechler et al. | 435/7.1 |
| 5,942,443 | A | | 8/1999 | Parce et al. | 436/514 |
| 5,948,227 | A | | 9/1999 | Dubrow | 204/455 |
| 5,955,028 | A | | 9/1999 | Chow | 422/63 |
| 5,957,579 | A | | 9/1999 | Kopf-Sill et al. | 366/340 |
| 5,958,203 | A | | 9/1999 | Parce et al. | 204/451 |
| 5,958,694 | A | | 9/1999 | Nikiforov | 435/6 |
| 5,959,291 | A | | 9/1999 | Jensen | 250/214 R |
| 5,964,995 | A | | 10/1999 | Nikiforov et al. | 204/450 |
| 5,965,001 | A | | 10/1999 | Chow et al. | 204/600 |
| 5,965,375 | A | | 10/1999 | Valkirs | 435/7.2 |
| 5,965,410 | A | | 10/1999 | Chow et al. | 435/91.2 |
| 5,972,187 | A | | 10/1999 | Parce et al. | 204/453 |
| 5,976,336 | A | | 11/1999 | Dubrow et al. | 204/453 |
| 5,985,579 | A | | 11/1999 | Buechler et al. | 435/7.1 |
| 5,989,402 | A | | 11/1999 | Chow et al. | 204/601 |
| 5,994,150 | A | | 11/1999 | Challener et al. | 436/518 |
| 6,001,231 | A | | 12/1999 | Kopf-Sill | 204/454 |
| 6,002,475 | A | | 12/1999 | Boyd et al. | 356/246 |
| 6,004,515 | A | | 12/1999 | Parce et al. | 422/100 |
| 6,011,252 | A | | 1/2000 | Jensen | 250/214 R |
| 6,012,902 | A | | 1/2000 | Parce | 417/48 |
| 6,019,944 | A | | 2/2000 | Buechler | 422/58 |
| 6,024,138 | A | | 2/2000 | Fritz et al. | 141/31 |
| 6,030,581 | A | | 2/2000 | Virtanen | 422/68.1 |
| 6,037,455 | A | | 3/2000 | Buechler | 530/404 |
| 6,042,709 | A | | 3/2000 | Parce et al. | 204/453 |
| 6,042,710 | A | | 3/2000 | Dubrow | 204/454 |
| 6,043,043 | A | | 3/2000 | Yip | 435/72 |
| 6,046,056 | A | | 4/2000 | Parce et al. | 436/514 |
| 6,048,498 | A | | 4/2000 | Kennedy | 422/99 |
| 6,063,589 | A | | 5/2000 | Kellogg et al. | 435/24 |
| 6,068,752 | A | | 5/2000 | Dubrow et al. | 204/604 |
| 6,071,478 | A | | 6/2000 | Chow | 422/81 |
| 6,074,616 | A | | 6/2000 | Buechler et al. | 422/104 |
| 6,074,725 | A | | 6/2000 | Kennedy | 428/188 |
| 6,080,295 | A | | 6/2000 | Parce et al. | 204/451 |
| 6,086,740 | A | | 7/2000 | Kennedy | 204/601 |
| 6,086,825 | A | | 7/2000 | Sundberg et al. | 422/100 |
| 6,090,251 | A | | 7/2000 | Sundberg et al. | 204/453 |
| 6,100,099 | A | | 8/2000 | Gordon et al. | 436/518 |
| 6,100,541 | A | | 8/2000 | Nagle et al. | 250/573 |
| 6,106,779 | A | | 8/2000 | Buechler et al. | 422/55 |
| 6,107,044 | A | | 8/2000 | Nikiforov | 435/6 |
| 6,113,855 | A | | 9/2000 | Buechler | 422/58 |
| 6,123,798 | A | | 9/2000 | Gandhi et al. | 156/292 |
| 6,129,826 | A | | 10/2000 | Nikiforov et al. | 204/450 |
| 6,130,098 | A | | 10/2000 | Handique et al. | |
| 6,132,685 | A | | 10/2000 | Kercso et al. | 422/104 |
| 6,136,610 | A | | 10/2000 | Polito et al. | 436/514 |
| 6,143,248 | A | | 11/2000 | Kellogg et al. | 422/72 |
| 6,143,576 | A | | 11/2000 | Buechler | 436/518 |
| 6,148,508 | A | | 11/2000 | Wolk | 29/825 |
| 6,149,870 | A | | 11/2000 | Parce et al. | 422/100 |
| 6,150,119 | A | | 11/2000 | Kopf-Sill et al. | 435/7.1 |
| 6,150,180 | A | | 11/2000 | Parce et al. | 436/514 |
| 6,156,270 | A | | 12/2000 | Buechler | 422/58 |
| 6,176,119 | B1 | | 1/2001 | Kintzig | 73/53.01 |
| 6,176,991 | B1 | | 1/2001 | Nordman | 204/601 |
| 6,185,029 | B1 | | 2/2001 | Ishihara | 359/216 |
| 6,207,000 | B1 | | 3/2001 | Schwobel et al. | 156/248 |
| 6,235,175 | B1 | | 5/2001 | Dubrow et al. | 204/453 |
| 6,238,538 | B1 | | 5/2001 | Parce et al. | 204/600 |
| 6,251,567 | B1 | | 6/2001 | Reinecke et al. | 430/325 |
| 6,254,754 | B1 | | 7/2001 | Ross et al. | 204/548 |
| 6,268,025 | B1 | | 7/2001 | Reinecke et al. | 427/581 |
| 6,271,040 | B1 | | 8/2001 | Buechler | 436/170 |
| 6,281,254 | B1 | | 8/2001 | Nakajima et al. | 516/53 |
| 6,284,113 | B1 | | 9/2001 | Bjornson et al. | 204/453 |
| 6,287,520 | B1 | | 9/2001 | Parce et al. | 422/100 |
| 6,296,020 | B1 | * | 10/2001 | McNeely et al. | 137/806 |
| 6,296,126 | B1 | | 10/2001 | Peters | 210/456 |
| 6,319,469 | B1 | | 11/2001 | Mian et al. | 422/64 |
| 6,321,791 | B1 | | 11/2001 | Chow | 137/833 |
| 6,322,683 | B1 | | 11/2001 | Wolk et al. | 204/600 |
| 6,379,974 | B1 | | 4/2002 | Parce et al. | 436/180 |
| 6,428,664 | B1 | | 8/2002 | Bhullar et al. | 204/403.03 |
| 6,540,896 | B1 | | 4/2003 | Manz et al. | 204/451 |
| 6,582,662 | B1 | | 6/2003 | Kellogg et al. | 422/72 |
| 6,632,399 | B1 | | 10/2003 | Kellogg et al. | 422/72 |
| 6,653,625 | B2 | | 11/2003 | Andersson et al. | 250/288 |
| 6,709,559 | B2 | | 3/2004 | Sundberg et al. | 204/604 |
| 6,734,401 | B2 | | 5/2004 | Bedingham et al. | 219/388 |
| 6,776,965 | B2 | | 8/2004 | Wyzgol et al. | 422/100 |
| 6,811,752 | B2 | | 11/2004 | Barbera-Guillem | 422/100 |
| 6,878,555 | B2 | | 4/2005 | Andersson et al. | 436/180 |
| 2001/0037099 | A1 | | 11/2001 | Effenhauser | 604/352 |
| 2001/0046453 | A1 | | 11/2001 | Land | 426/521 |
| 2002/0023684 | A1 | | 2/2002 | Chow | 137/833 |
| 2002/0112961 | A1 | | 8/2002 | O'Connor et al. | 204/601 |
| 2002/0114738 | A1 | | 8/2002 | Wyzgol et al. | 422/100 |

FOREIGN PATENT DOCUMENTS

| | | | |
|---|---|---|---|
| EP | 0287 883 | A1 | 10/1988 |
| EP | 0 693 560 | A1 | 1/1996 |
| EP | 0693560 | A2 | 1/1996 |
| EP | 1 013 341 | A3 | 1/2001 |
| EP | 1 013 341 | B1 | 12/2003 |
| WO | WO 95/17965 | A1 | 7/1995 |
| WO | WO 97/01055 | | 1/1997 |
| WO | WO 99/46045 | A1 | 9/1999 |
| WO | WO 00/21728 | | 4/2000 |
| WO | WO 00/22436 | | 4/2000 |
| WO | WO 00/22436 | A1 | 4/2000 |
| WO | WO 00/25921 | | 5/2000 |
| WO | WO 00/34781 | A2 | 6/2000 |
| WO | WO 00/34781 | A3 | 6/2000 |
| WO | WO 00/36416 | A1 | 6/2000 |

| | | | |
|---|---|---|---|
| WO | WO 01/12329 | A1 | 2/2001 |
| WO | WO 01/14063 | A1 | 3/2001 |
| WO | WO 01/14116 | A1 | 3/2001 |
| WO | WO 01/19586 | A1 | 3/2001 |
| WO | WO 01/24931 | A1 | 4/2001 |
| WO | WO 01/54810 | A1 | 8/2001 |
| WO | WO 02/18053 | A1 | 3/2002 |
| WO | WO 02/28532 | A2 | 4/2002 |
| WO | WO 02/28532 | A3 | 4/2002 |

* cited by examiner

METHOD AND APPARATUS FOR PRECISE TRANSFER AND MANIPULATION OF FLUIDS BY CENTRIFUGAL AND/OR CAPILLARY FORCES

BACKGROUND OF THE INVENTION

This invention relates generally to the field of microfluidics, as applied to analysis of various biological and chemical compositions. More particularly, the invention provides methods and apparatus for carrying out analyses, using both imposed centrifugal forces and capillary forces resulting from the surface properties of the passageways in the apparatus To determine the presence (or absence) of, or the amount of an analyte, such as glucose, albumin, or bacteria in bodily or other fluids, a reagent device is generally used to assist a technician performing the analysis. Such reagent devices contain one or more reagent areas at which the technician can apply the sample fluid and then compare the result to a standard. For example, a reagent strip is dipped into the sample fluid and the strip changes color, the intensity or type of color being compared with a standard reference color chart.

Preparation of such devices is difficult when the sample has a complex composition, as many bodily fluids do. The component to be identified or measured may have to be converted to a suitable form before it can be detected by a reagent to provide a characteristic color. Other components in the sample fluid may interfere with the desired reaction and they must be separated from the sample or their effect neutralized. Sometimes, the reagent components are incompatible with each other. In other cases, the sample must be pretreated to concentrate the component of interest. These and other problems make it difficult to provide in a single device the reagent components which are needed for a particular assay. The art contains many examples of devices intended to overcome such problems and to provide the ability to analyze a fluid sample for a particular component or components.

A different approach is to carry out a sequence of steps which prepare and analyze a sample, but without requiring a technician to do so. One way of doing this is by preparing a device which does the desired processes automatically, but by keeping the reagents isolated, is able to avoid the problems just discussed. For small samples, such analyses may employ microfluidic techniques.

Microfluidic devices are small, but they can receive a sample, select a desired amount of the sample, dilute or wash the sample, separate it into components, and carry out reactions with the sample or its components. If one were to carry out such steps in a laboratory on large samples, it would generally be necessary for a technician to manually perform the necessary steps or if automated, equipment would be needed to move the sample and its components and to introduce reagents, wash liquids, diluents and the like. However, it is typical of biological assays that the samples are small and therefore it follows that the processing steps must be carried out in very small equipment. Scaling down laboratory equipment to the size needed for samples of about 0.02 to 10.0 μL is not feasible and a different approach is used. Small vessels connected by μm size passageways are made by creating such features in plastic or other suitable substrates and covering the resulting substrate with another layer. The vessels may contain reagents added to them before the covering layer is applied. The passageways may also be treated as desired to make them wettable or non-wettable by the sample to be tested. The sample, its components, or other fluids may move through such passageways by capillary action when the walls are wetted or they are prevented from moving when the fluids do not wet the walls of the passageway. Thus, the capillary sized passageways can either move fluids or prevent their movement as if a valve were present. Another method of moving fluids through such μm sized passageways is by centrifugal force, which overcomes the resistance of non-wettable walls. This simple description provides an overview of microfluidic devices. Specific applications are provided in many patents, some of which will be mentioned below.

An extended discussion of some of the principles used in arranging the vessels and passageways for various types of analyses is provided in U.S. Pat. No. 6,143,248 and additional examples of applications of those principles may be found in U.S. Pat. No. 6,063,589. The microfluidic devices described in those two patents were intended to be disposed in disc form and rotated on equipment capable of providing varying degrees of centrifugal force as needed to move fluids from one vessel to another. Generally, a sample would be supplied close to the center of rotation and gradually increasing rotational speeds would be used to move the sample, or portions of it, into vessels disposed further away from the center of rotation. The patents describe how specific amounts of samples can be isolated for analysis, how the samples can be mixed with other fluids for washing or other purposes, and how samples can be separated into their components.

Other patents describe the use of electrodes for moving fluids by electro-osmosis, such as U.S. Pat. No. 4,908,112. Caliper Technology Corporation has a portfolio of patent on microfluidic devices in which fluids are moved by electromotive propulsion. Representative examples are U.S. Pat. Nos. 5,942,443; 5,965,001; and 5,976,336.

In U.S. Pat. No. 5,141,868 capillary action is used to draw a sample into a cavity where measurements of the sample can be made by electrodes positioned in the sample cavity.

The present inventors have also been concerned with the need to provide reagent devices for immunoassays and nucleic acid assays, for example the detection of bacterial pathogens, proteins, drugs, metabolites and cells. Their objective has been to overcome the problems involved when incompatible components are required for a given analytical procedure and pre-treatment of the sample is needed before an analysis can be carried out. Their solution to such problems differs from those previously described and is described in detail below.

SUMMARY OF THE INVENTION

The invention may be generally characterized as analytical device which employs microfluidic techniques to provide analyses of small biological samples in an improved manner. The device of the invention also makes possible analyses which have not been possible heretofore with conventional analytical strips.

The analytical device of the invention may be referred to herein as a "chip" in that it typically is a small piece of thin plastic into which has been cut microliter sized wells for receiving sample liquids, the wells being interconnected by capillary passageways having a width of about 10 to 500 μm and a depth of at least 5 μm. The passageways may be made either hydrophobic or hydrophilic using known methods, preferably by plasma polymerization at the walls. The degree of hydrophobicity or hydrophilicity is adjusted as required by the properties of the sample fluid to be tested. In some embodiments, the hydrophobic surfaces are adjusted to prevent deposits from adhering to the walls. In other embodiments, the hydrophilic surfaces are adjusted to provide substantially complete removal of the liquid.

Two types of capillary stops are disclosed, a narrow stop having hydrophobic walls and a wide stop having hydrophilic walls. The desired features are formed in a base portion of the chip, reagents are placed in the appropriate wells and then a top portion is applied to complete the chip.

In some embodiments, an analytical chip of the invention includes a defined segment of a hydrophilic capillary connected to the well in which a sample fluid is placed. The sample fluid fills the segment by capillary action and thus provides a fixed volume of the sample for subsequent transfer to other wells for the desired analysis. In some embodiments, the defined capillary segment is in the form of a U-shaped loop vented to the atmosphere at each end. In other embodiments, the defined capillary segment is linear.

By using multiple wells connected by capillary passageways, sample fluids can be provided with many separate treatments in a predetermined sequence, thereby avoiding many of the problems which are difficult to overcome with conventional test strips. For example, sample fluids can be washed or pretreated before being brought into contact with a suitable reagent. More than one reagent may be used with a single sample in sequential reactions. Also, liquids can be removed from a sample after a reaction has occurred in order to improve the accuracy of the measurements made on the reacted sample. These and other possible configurations of typical devices of the invention are illustrated in the Figures and description below.

DESCRIPTION OF THE PREFERRED EMBODIMENTS

Flow in Microchannels

Figure 1:
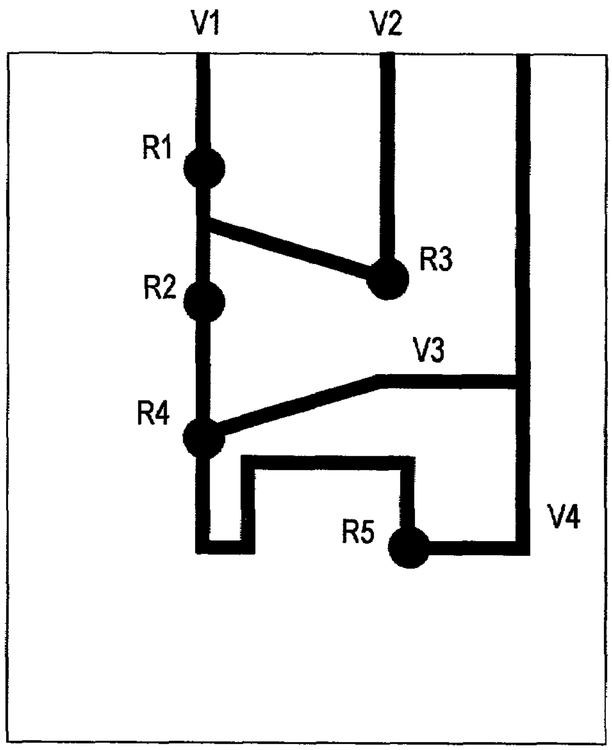
FIG. 1 is one analytical device of the invention.

The devices employing the invention typically use smaller channels than have been proposed by previous workers in the field. In particular, the channels used in the invention have widths in the range of about 10 to 500 μm, preferably about 20-100 μm, whereas channels an order of magnitude larger have typically been used by others. The minimum dimension for such channels is believed to be about 5 μm since smaller channels may effectively filter out components in the sample being analyzed. Generally, the depth of the channels will be less than the width. It has been found that channels in the range preferred in the invention make it possible to move liquid samples by capillary forces without the use of centrifugal force except to initiate flow. For example, it is possible to stop movement by capillary walls which are treated to become hydrophobic relative to the sample fluid. The resisting capillary forces can be overcome by application of centrifugal force, which can then be removed as liquid flow is established. Alternatively, if the capillary walls are treated to become hydrophilic relative to the sample fluid, the fluid will flow by capillary forces without the use of centrifugal or other force. If a hydrophilic stop is included in such a channel, then flow will be established through application of a force to overcome the effect of the hydrophilic stop. As a result, liquids can be metered and moved from one region of the device to another as required for the analysis to be carried out.

A mathematical model has been derived which relates the centrifugal force, the fluid physical properties, the fluid surface tension, the surface energy of the capillary walls, the capillary size and the surface energy of particles contained in fluids to be analyzed. It is possible to predict the flow rate of a fluid through the capillary and the desired degree of hydrophobicity or hydrophilicity. The following general principles can be drawn from the relationship of these factors.

For any given passageway, the interaction of a liquid with the surface of the passageway may or may not have a significant effect on the movement of the liquid. When the surface to volume ratio of the passageway is large i.e. the cross-sectional area is small, the interactions between the liquid and the walls of the passageway become very significant. This is especially the case when one is concerned with passageways with nominal diameters less than about 200 μm, when capillary forces related to the surface energies of the liquid sample and the walls predominate. When the walls are wetted by the liquid, the liquid moves through the passageway without external forces being applied. Conversely, when the walls are not wetted by the liquid, the liquid attempts to withdraw from the passageway. These general tendencies can be employed to cause a liquid to move through a passageway or to stop moving at the junction with another passageway having a different cross-sectional area. If the liquid is at rest, then it can be moved by applying a force, such as the centrifugal force. Alternatively other means could be used, including air pressure, vacuum, electroosmosis, and the like, which are able to induce the needed pressure change at the junction between passageways having different cross-sectional areas or surface energies. It is a feature of the present invention that the passageways through which liquids move are smaller than have been used heretofore. This results in higher capillary forces being available and makes it possible to move liquids by capillary forces alone, without requiring external forces, except for short periods when a capillary stop must be overcome. However, the smaller passageways inherently are more likely to be sensitive to obstruction from particles in the biological samples or the reagents. Consequently, the surface energy of the passageway walls is adjusted as required for use with the sample fluid to be tested, e.g. blood, urine, and the like. This feature allows more flexible designs of analytical devices to be made. The devices can be smaller than the disks which have been used in the art and can operate with smaller samples. Other advantages will become evident from the description of the devices and the examples.

Analytical Devices of the Invention

The analytical devices of the invention may be referred to as "chips". They are generally small and flat, typically about 1 to 2 inches square (25 to 50 mm square). The volume of samples will be small. For example, they will contain only about 0.3 to 1.5 μL and therefore the wells for the sample fluids will be relatively wide and shallow in order that the samples can be easily seen and measured by suitable equipment. The interconnecting capillary passageways will have a width in the range of 10 to 500 μm, preferably 20 to 100 μm, and the shape will be determined by the method used to form the passageways. The depth of the passageways should be at least 5 μm. When a segment of a capillary is used to define a predetermined amount of a sample, the capillary may be larger than the passageways between reagent wells.

While there are several ways in which the capillaries and sample wells can be formed, such as injection molding, laser ablation, diamond milling or embossing, it is preferred to use injection molding in order to reduce the cost of the chips. Generally, a base portion of the chip will be cut to create the desired network of sample wells and capillaries and then a top portion will be attached over the base to complete the chip.

The chips are intended to be disposable after a single use. Consequently, they will be made of inexpensive materials to the extent possible, while being compatible with the reagents and the samples which are to be analyzed. In most instances, the chips will be made of plastics such as polycarbonate, polystyrene, polyacrylates, or polyurethene, alternatively, they can be made from silicates, glass, wax or metal.

The capillary passageways will be adjusted to be either hydrophobic or hydrophilic, properties which are defined with respect to the contact angle formed at a solid surface by a liquid sample or reagent. Typically, a surface is considered hydrophilic if the contact angle is less than 90 degrees and hydrophobic if the contact angle is greater. A surface can be treated to make it either hydrophobic or hydrophilic. Preferably, plasma induced polymerization is carried out at the surface of the passageways. The analytical devices of the invention may also be made with other methods used to control the surface energy of the capillary walls, such as coating with hydrophilic or hydrophobic materials, grafting, or corona treatments. In the present invention, it is preferred that the surface energy of the capillary walls is adjusted, i.e. the degree of hydrophilicity or hydrophobicity, for use with the intended sample fluid. For example, to prevent deposits on the walls of a hydrophobic passageway or to assure that none of the liquid is left in a passageway.

Movement of liquids through the capillaries is prevented by capillary stops, which, as the name suggests, prevent liquids from flowing through the capillary. If the capillary passageway is hydrophilic and promotes liquid flow, then a hydrophobic capillary stop can be used, i.e. a smaller passageway having hydrophobic walls. The liquid is not able to pass through the hydrophobic stop because the combination of the small size and the non-wettable walls results in a surface tension force which opposes the entry of the liquid. Alternatively, if the capillary is hydrophobic, no stop is necessary between a sample well and the capillary. The liquid in the sample well is prevented from entering the capillary until sufficient force is applied, such as by centrifugal force, to cause the liquid to overcome the opposing surface tension force and to pass through the hydrophobic passageway. It is a feature of the present invention that the centrifugal force is only needed to start the flow of liquid. Once the walls of the hydrophobic passageway are fully in contact with the liquid, the opposing force is reduced because presence of liquid lowers the energy barrier associated with the hydrophobic surface. Consequently, the liquid no longer requires centrifugal force in order to flow. While not required, it may be convenient in some instances to continue applying centrifugal force while liquid flows through the capillary passageways in order to facilitate rapid analysis.

When the capillary passageways are hydrophilic, a sample liquid (presumed to be aqueous) will naturally flow through the capillary without requiring additional force. If a capillary stop is needed, one alternative is to use a narrower hydrophobic section which can serve as a stop as described above. A hydrophilic stop can also be used, even through the capillary is hydrophilic. Such a stop is wider than the capillary and thus the liquid's surface tension creates a lower force promoting flow of liquid. If the change in width between the capillary and the wider stop is sufficient, then the liquid will stop at the entrance to the capillary stop. It has been found that the liquid will eventually creep along the hydrophilic walls of the stop, but by proper design of the shape this movement can be delayed sufficiently so that stop is effective, even though the walls are hydrophilic. A preferred hydrophilic stop is illustrated in FIG. 3*b*, along with a hydrophobic stop (3*a*) previously described.

FIG. 1 shows a test device embodying aspects of the invention. A specimen e.g. of urine, is placed in the reagent well R1. In this device all of the passageways have been treated by plasma polymerization to be hydrophobic so that the liquid sample does not move through the passageway to R2 without application of an external force. When the device is placed on a platform and rotated at the proper speed to overcome the hydrophobic forces, the sample liquid can move into R2 where it can be reacted or otherwise prepared for subsequent analysis. R3 will receive liquid also during the period when R2 is being filled so that the sample added to R1 may be greater than can be accepted by R2. R3 could provide a second reaction of a portion of the sample, or merely provide an overflow for the excess sample. Alternatively, R3 could deliver a pretreated portion of the sample to R2 if desired. Since the passageway between R2 and R4 is also hydrophobic, additional centrifugal force must be applied to move the sample liquid. With added centrifugal force, R5 could be filled with the reacted sample from R4 or could be used to receive the liquid remaining after the analyte had been reacted in R4 and retained there. Such a step could provide improved ability to measure the reaction product in R4, if it would otherwise be obscured by materials in the liquid. In the design of FIG. 1, there are no capillary stops provided, because the capillary passageways were made hydrophobic. However, if the passageways had been hydrophilic, capillary stops would be provided at the outlet of R1, R2, and R 4, thus preventing the liquid from moving through the capillary passageways until sufficient centrifugal force was applied to overcome the stop, after which the capillary forces would operate to move the sample liquid and further centrifugal force would not be needed. That is, the capillary forces alone would be sufficient to move the sample liquid. It should be noted that each of the wells R1, R3, R4, and R5 have a passageway open to the ambient pressure (V1, V2, V3 and V4) so that gases in the wells can be vented while the sample liquid is filling the wells.

Figure 2:
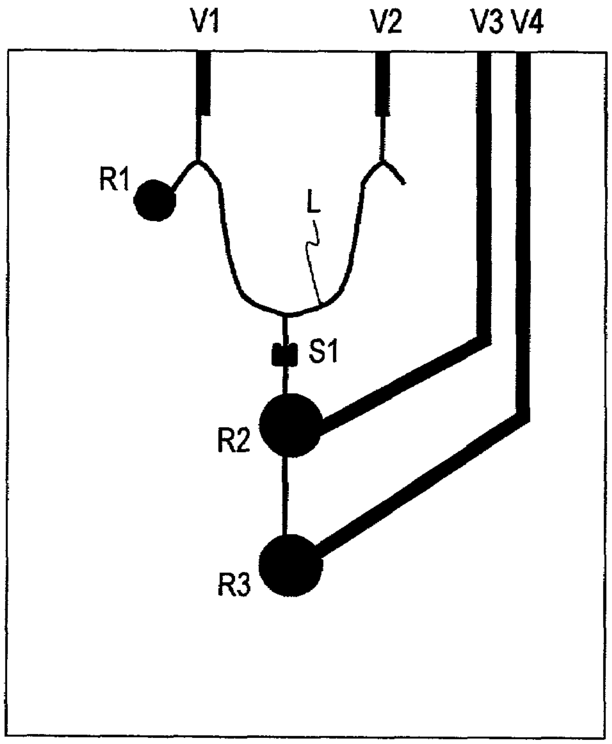
FIG. 2 is a second analytical device of the invention.

FIG. 2 shows a second test device which incorporates a metering capillary segment and a hydrophilic stop. The metering segment assures that a precise amount of a liquid sample is dispensed, so that the analytical accuracy is improved. A sample of liquid is added to sample well R1, from which it flows by capillary forces (the passageways are hydrophilic) and fills the generally U-shaped metering loop L. The shape of the metering loop or segment of the capillary need not have the shape shown. Straight or linear capillary segments can be used instead. The ends of the loops are vented to the atmosphere via V1 and V2. The sample liquid moves as far as the hydrophilic stop S1 (would also be a hydrophobic stop if desired). When the device is placed on a platform and rotated at a speed sufficient to overcome the resistance of the hydrophilic stop, the liquid contained in the sample loop L passes the stop S1 and moves by capillary forces into the reagent well R2. Air enters the sample loop as the liquid moves out, thus breaking the liquid at the air entry points V1 and V2 which define the length of the liquid column and thus the amount of the sample delivered to the reagent well R2. Below the sample loop is an additional reagent well R3, which can be used to react with the sample liquid or to prepare it for subsequent analysis, as will be discussed further below. The liquid will move from R2 to R3 by capillary forces since the walls are hydrophilic. If the capillary walls were hydrophobic, the liquid would not flow into R3 until the opposing force is overcome by application of centrifugal force.

Figure 3A:
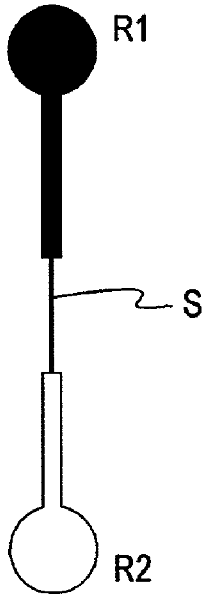
FIGS. 3*a*& *b* illustrate hydrophobic and hydrophilic capillary stops.
Figure 3B:
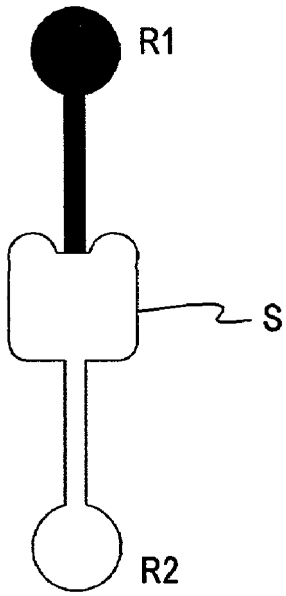

FIGS. 3*a* & *b* illustrate a hydrophobic stop (a) and a hydrophilic stop (b) which may be used in analytical devices of the invention. In FIG. 3*a* well R1 is filled with liquid and the liquid extends through the attached hydrophilic capillary until the liquid is prevented from further movement by the narrow hydrophobic capillary passageways, which provide a surface tension force which prevents the liquid from entering the stop. If a force is applied from well R1 in the direction of the capillary stop the opposing force can be overcome and the liquid in R1 can be transferred to well R2. Similarly, in FIG. 3*b* the capillary stop illustrated is a hydrophilic stop, which prevents the liquid in R1 from flowing through into well R2. In this case, the capillary stop is not narrow and it has hydrophilic walls. The increase in width of the channel and the shape of the stop prevent surface tension forces from causing liquid flow out of the attached capillary. However, as mentioned above, it has been found that liquid will gradually creep along the walls and overcome the stopping effect with the passage of enough time. For most analytical purposes, the stop serves its purpose since the time needed for analysis of a sample is short compared to the time needed for the liquid to overcome the stop by natural movement of the liquid.

Figure 4A:
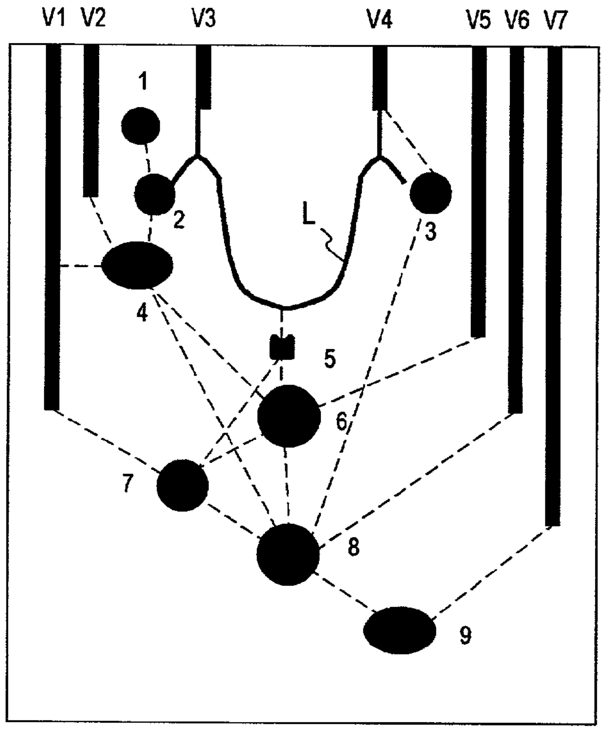
FIG. 4*a* illustrates a multi-purpose analytical device of the invention.

FIG. 4*a* shows the plan view of a multi-purpose analytical chip of the invention. Vent channels V1-V7, wells 1-4 and 6-9, capillary stop 5, and a U-shaped sample loop L are formed in the chip, with dotted lines illustrating possible capillary passageways which could be formed in the chip base before a top cover is installed. As will be evident, many possible configurations are possible. In general, a sample liquid would be added to well R2 so that the sample loop can be filled by capillary forces and dispensed through capillary stop 5 into wells 6-8 where the sample would come into contact with reagents and a response to the reagents would be measured. Wells 1 and 3 would be used to hold additional sample liquid or alternatively, another liquid for pretreating the sample. Wells 4 and 9 would usually serve as chambers to hold waste liquids or, in the case of well 4 as an overflow for sample liquid from well 2 or a container for a wash liquid. Each of the wells can be vented to the appropriate vent channel as required for the analysis to be carried out. Some of the possible configurations are shown in FIGS. 4 *b*-*i*.

In each of FIG. 4*b*-*j*, only some of the potential capillary passageways have been completed, the remaining capillaries and wells are not used. The vent connections shown in FIG. 4*a* are not shown to improve clarity, but it should be understood that they will be provided if required for the analysis to be carried out.

Figure 4B:
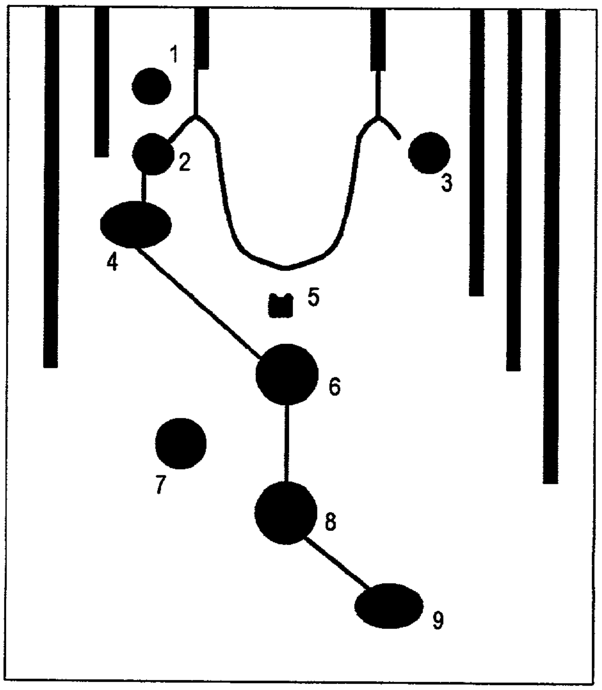
FIGS. 4*b-j* show representative configurations which can be provided using the multi-purpose device of FIG. 4*a*.

In FIG. 4*b*, a sample liquid is added to well 2, which flows into well 4 through the hydrophobic capillary when the resistance to flow is overcome by applying sufficient centrifugal force (alternatively other means of opposing the force resisting flow could be used). Similarly, the sample can be moved in sequence through wells 6, 8, and 9 by increasing the centrifugal force to overcome the initial resistance presented by the connecting hydrophobic capillaries. Wells 4, 6, 8, and 9 may contain reagents as required by a desired analytical procedure.

Figure 4C:
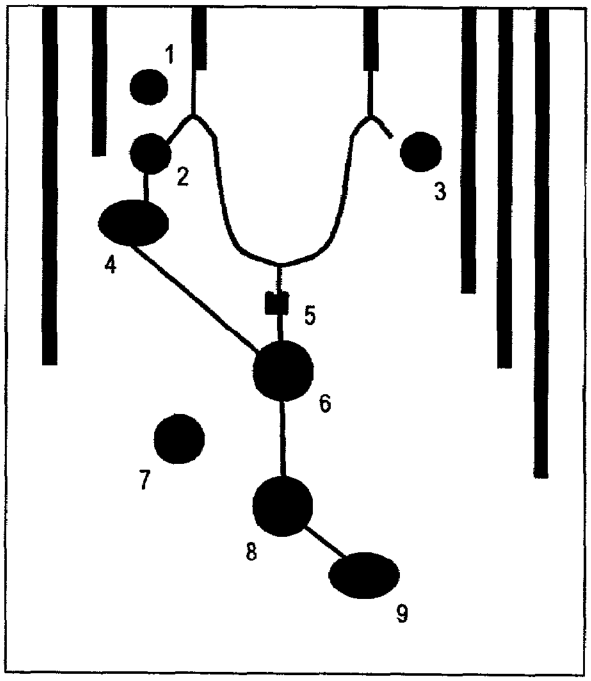

FIG. 4*c* provides the ability to dispense a metered amount of a liquid sample from the loop L through the hydrophilic stop 5, the resistance of which is overcome by applying a suitable amount of centrifugal force. Alternatively, additional sample can be transferred to well 4 where it is treated by a reagent before being transferred to well 6. From well 6, the sample can be transferred to wells 8 and 9 in sequence by increasing centrifugal force to overcome the resistance of the hydrophobic capillaries. Depending on the particular analysis, wells 6, 8, and 9 could be used to allow binding reactions to occur between a molecule in a specimen and a binding partner in the reagent well such as antibody to antigen, nucleotide to nucleotide or host to guest reaction. In addition, the binding pair can be conjugated to detection labels or tags.

The wells may also be used to capture (trap) antibody, nucleotide or antigen in the reagent well using binding partners immobilized to particles and surfaces; to wash or react away impurities, unbound materials or interferences; or to add reagents to for calibration or control of the detection method.

One of the wells typically will generate and/or detect a signal through a detection method included in the well. Examples of which include electrochemical detection, spectroscopic detection, magnetic detection and the detection of reactions by enzymes, indicators or dyes.

Figure 4D:
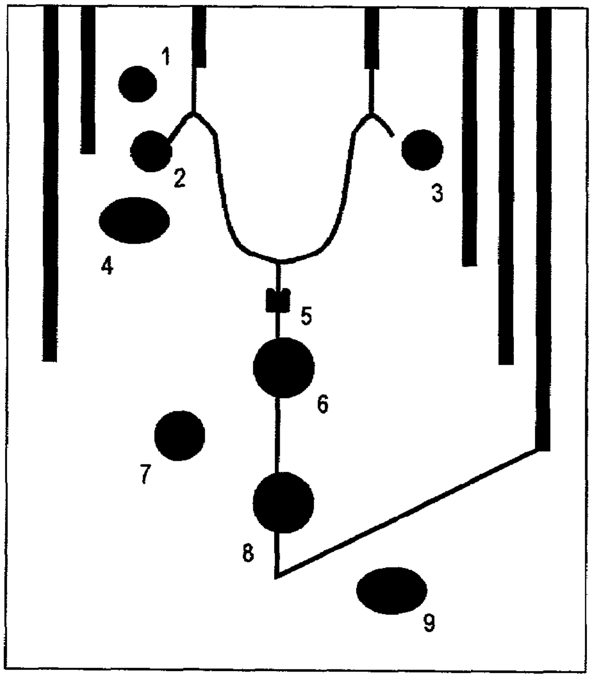

FIG. 4*d* provides means to transfer a metered amount of a sample fluid from well 2 via metering loop L and hydrophilic stop 5 to wells 6 and 8 in sequence. The sample may be concentrated in well 6 or separated as may be needed for immunoassay and nucleic acid assays, before being transferred to well 8 for further reaction. In this variant, it is possible to transfer the liquid from well 8 into one of the vent channels.

Figure 4E:
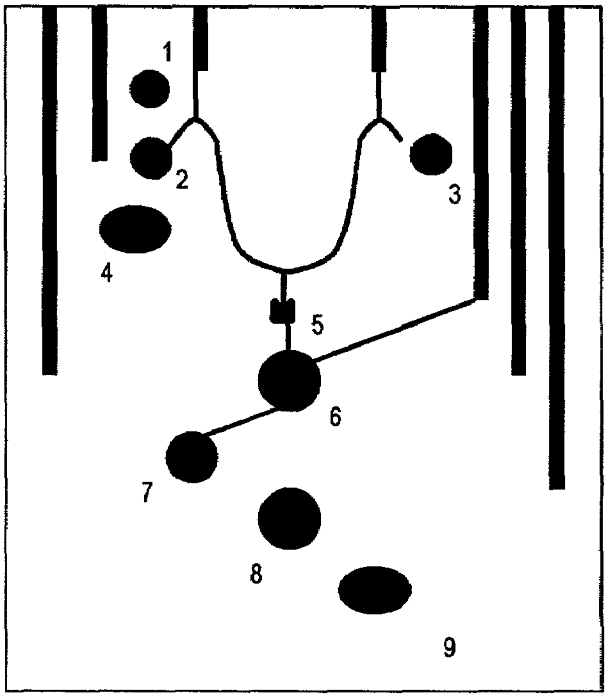

FIG. 4*e* is similar to FIG. 4*d* except that wells 6 and 7 are used rather than wells 6 and 8. This variant also illustrates that a linear arrangement is not necessary in order to transfer liquid from well 6.

Figure 4F:
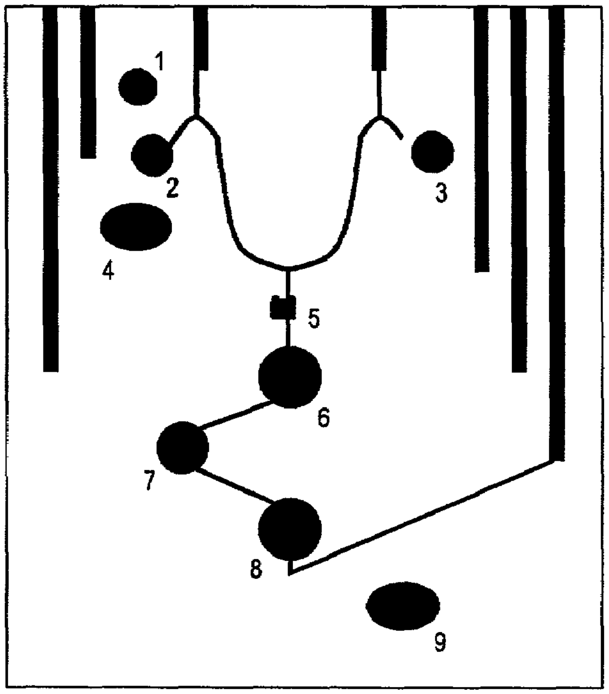

FIG. 4*f* is similar to FIGS. 4*d* and *e* in that a sample is transferred in sequence through wells 6, 7, and 8.

Figure 4G:
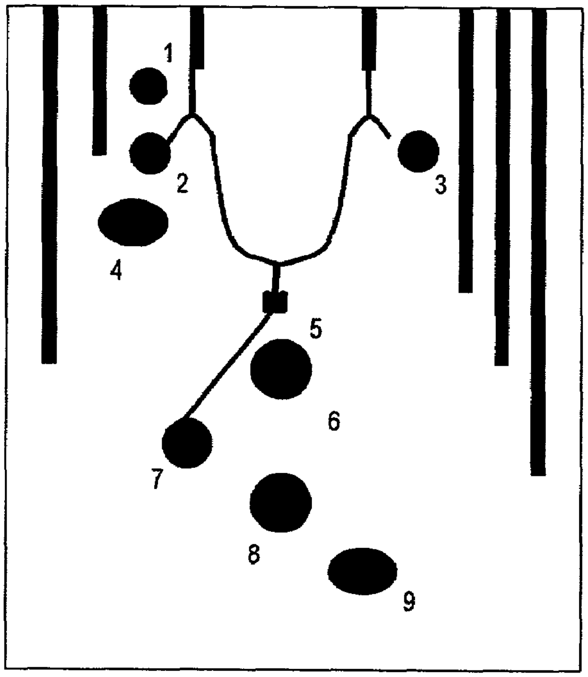

FIG. 4*g* is a variant in which the metered sample is transferred to well 7 rather than well 6 as in FIGS. 4*c*-*e*.

Figure 4H:
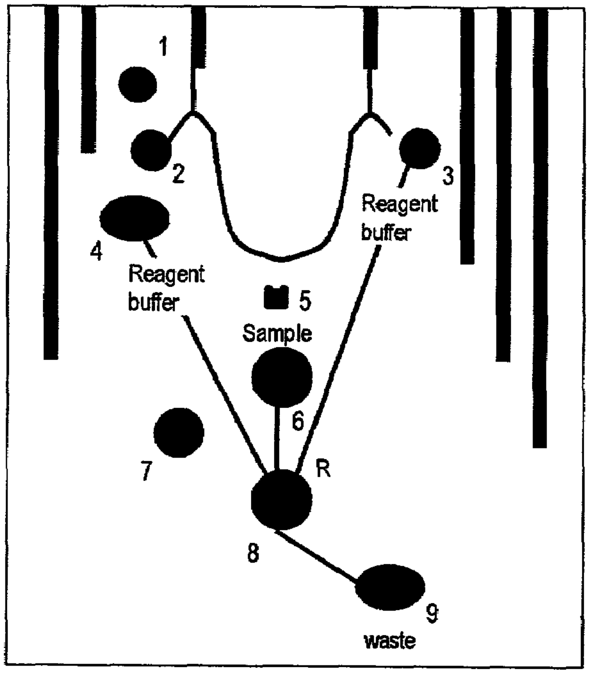

FIG. 4*h* illustrates a chip in which the sample fluid is added to well 6 and transferred to well 8 by applying sufficient force to overcome the resistance of the hydrophobic passageway. In well 8 reagents or buffers are added from wells 3 and 4 as needed for the analysis being carried out. Waste liquid is transferred to well 9, which may be beneficial to improve the accuracy of the reading of the results in well 8.

Figure 4I:
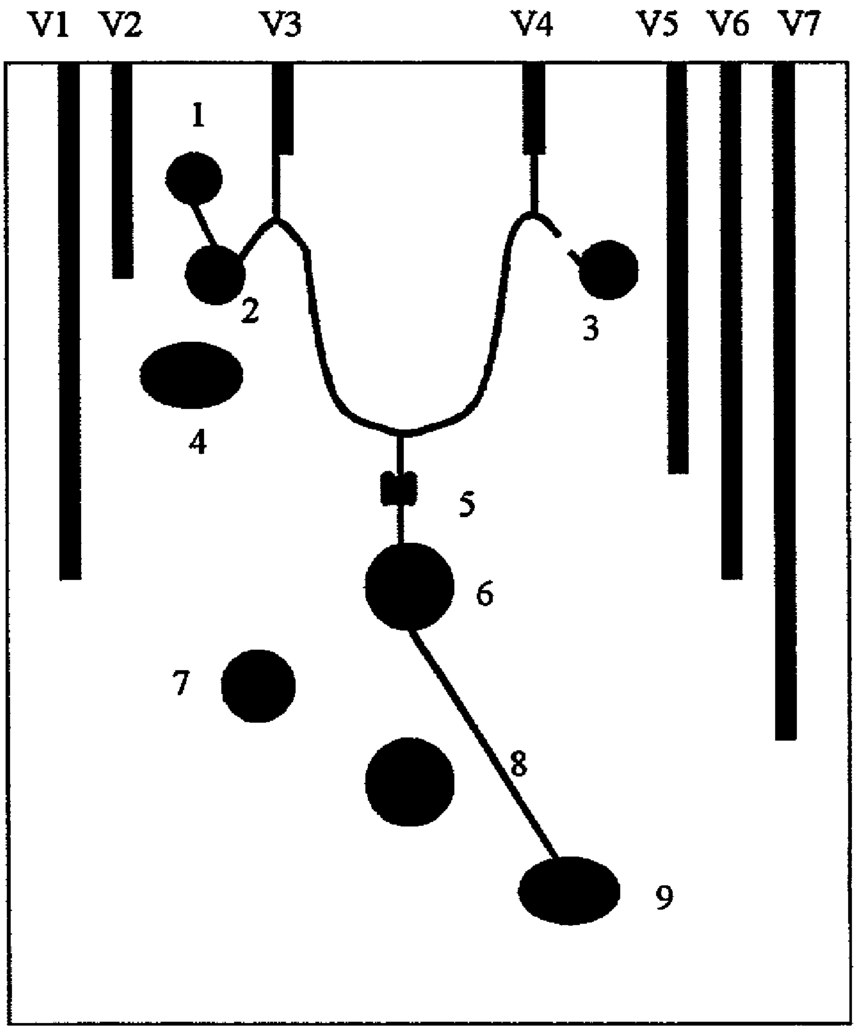

FIG. 4*i* illustrates a chip in which a fluid sample is introduced to well 1 and transferred to well 2 where it is pre-treated before entering the metering loop as previously described. Subsequently, a metered amount of the pre-treated sample is dispensed to well 6 by overcoming the hydrophilic stop 5 with the application of centrifugal force. As in previous examples, the sample can be transferred to other well, in this case well 9, for further processing by overcoming the resistance of the connecting hydrophobic capillary.

Figure 4J:
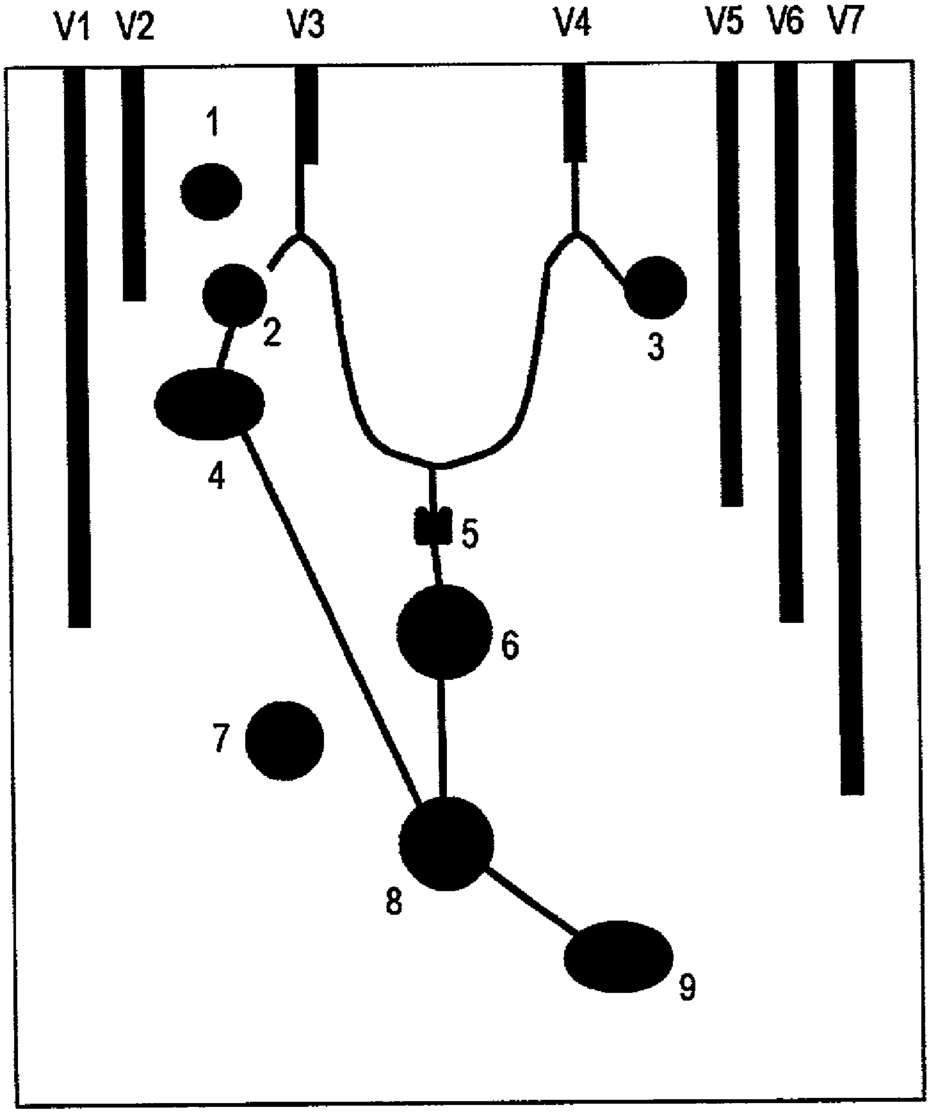

FIG. 4j illustrates a device in which a sample is added to well 3 instead of well 2. Well 2 receives a wash liquid, which is transferred to well 4 by overcoming the hydrophobic forces in the connecting passageway. Well 6 receives a metered amount of the sample from the U-shaped segment by overcoming the resistance of the hydrophilic stop 5. A reaction may be carried out in well 6, after which the sample is transferred to well 8 where it is further reacted and then washed by the wash liquid transferred from well 4 to well 8 and thereafter to well 9. The color developed in well 8 is then read.

Figure 5:
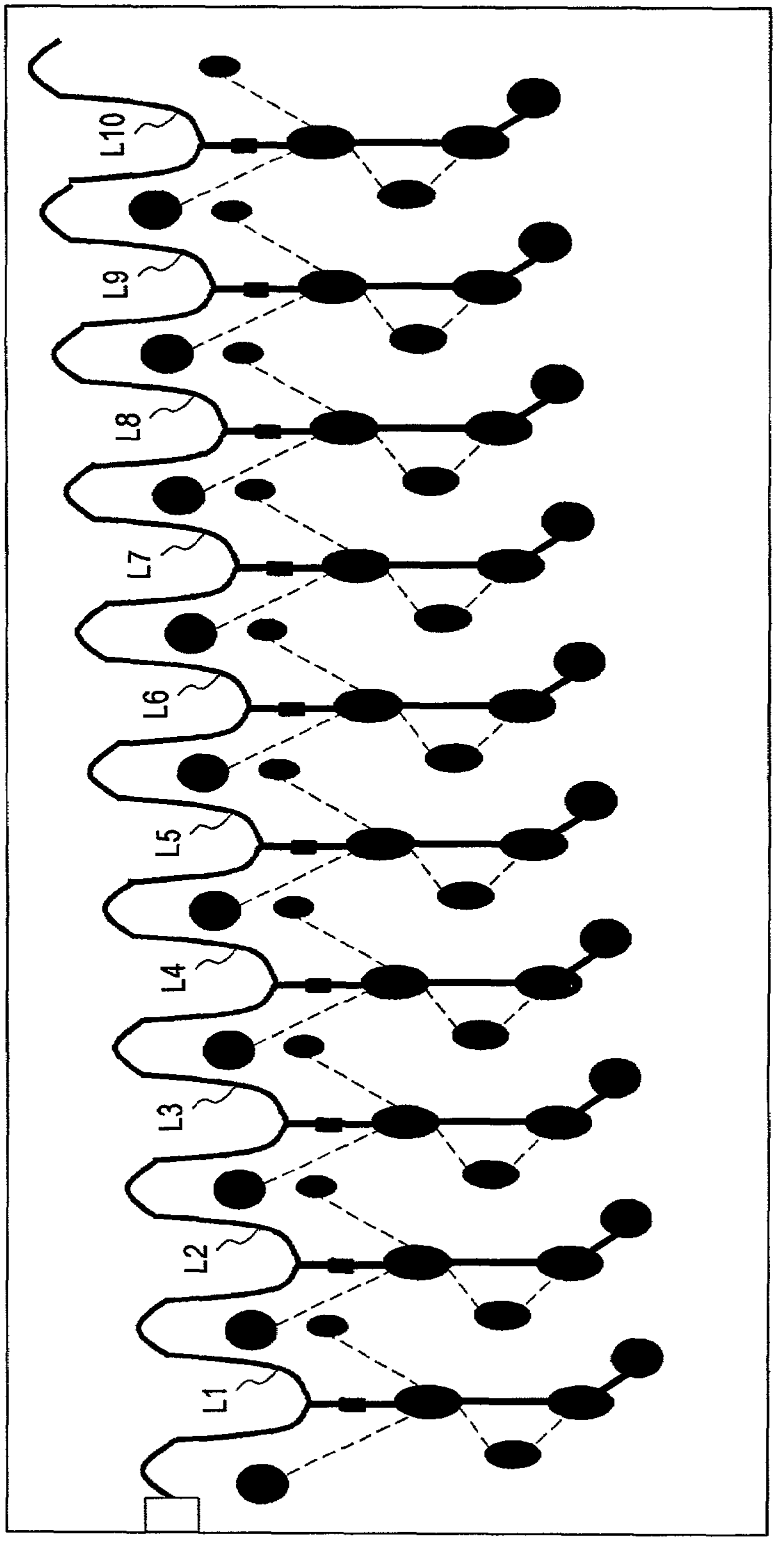
FIG. 5 illustrates an analytical device in which up to ten samples can be analyzed.

FIG. 5 shows a variation of the chips of the invention in which a single sample of liquid is introduced at sample well S, from which it flows by capillary forces through hydrophilic capillaries into ten sample loops L 1-10 of the type previously described. It will be understood that instead of ten sample loops any number could be provided, depending on the size of the chip. The vent channels are not illustrated in FIG. 5, but it will be understood that they will be present. The liquid is stopped in each loop by hydrophilic stops. Then, when a force is applied to overcome the capillary stops, the liquid can flow into the wells for analysis. As in FIG. 4, a number of possible arrangements of the capillary channels can be created.

In many applications, color developed by the reaction of reagents with a sample is measured, as is described in the examples below. It is also feasible to make electrical measurements of the sample, using electrodes positioned in the small wells in the chip. Examples of such analyses include electrochemical signal transducers based on amperometric, impedimetric, potentimetric detection methods. Examples include the detection of oxidative and reductive chemistries and the detection of binding events.

EXAMPLE 1

A reagent for detecting Hemoglobin was prepared by first preparing aqueous and ethanol coating solutions of the following composition.

| Component | Concentration mM |
|---|---|
| Aqueous coating solution: | |
| Glycerol-2-phosphate | 200 |
| Ferric chloride | 5.1 |
| N(2-hydroxyethyl)ethylenediamine triacetic acid | 5.1 |
| Triisopropanol amine | 250 |
| Sodium Dodecyl Sulfate [SDS] | 28 |
| Adjust pH to 6.4 with 1 N HCl | |

-continued

| Component | Concentration mM |
|---|---|
| Ethanol coating solution: | |
| Tetramethylbenzidine [TMB] | 34.7 |
| Diisopropylbenzene dihydroperoxide [DBDH] | 65.0 |
| 4-Methylquinoline | 61.3 |
| 4-(4-Diethylaminophenylazo) benzenesulfonic acid | 0.69 |
| 4-(2-Hydroxy-(7,9-sodiumdisulfonate)-1-naphthylazo)benzene | 0.55 |

The aqueous coating solution was applied to filter paper (3MM grade from Whatman Ltd) and the wet paper dried at 90° C. for 15 minutes. The dried reagent was then saturated with the ethanol coating solution followed by drying again at 90° C. for 15 minutes.

A reagent for detecting albumin was prepared by first preparing aqueous and toluene coating solutions of the following composition:

| Component | | Concentration mM | Allowable Range |
|---|---|---|---|
| Aqueous coating solution: | | | |
| Water | Solvent | 1000 mL | — |
| Tartaric acid | Cation Sensing Buffer | 93.8 g (625 mM) | 50-750 mM |
| Quinaldine red | Background dye | 8.6 mg (20 mM) | 10-30 mM |
| Toluene coating solution: | | | |
| Toluene | Solvent | 1000 mL | — |
| DIDNTB | Buffer | 0.61 g (0.6 mM | 0.2-0.8 mM |
| Lutonal M40 | Polymer enhancer | 1.0 g | 0.5-4 g/L |

DIDNTB = 5',5''-Dinitro-3',3''-Diiodo-3,4,5,6-Tetrabromophenolsulfonephthalein

The coating solutions were used to saturate filter paper, in this case 204 or 237 Ahlstrom filter paper, and the paper was dried at 95° C. for 5 minutes after the first saturation with the aqueous solution and at 85° C. for 5 minutes after the second saturation with the toluene solution.

Test solutions where prepared using the following formulas. Proteins were weighed out and added to MAS solution source. MAS solution is a phosphate buffer designed to mimic the average and extreme properties of urine. Natural urine physical properties are shown in the table below.

TABLE A

| | | density | viscosity | surface tension 10E−3 N/m or dyn/cm | Freezing Point ° C. Depression | Osmolality mmol/kg | pH | dry mass g/L |
|---|---|---|---|---|---|---|---|---|
| extreme | LOW | 1.001 | 1 | 64 | 0.1 | 50 | 4.5 | 50 |
| range | HIGH | 1.028 | 1.14 | 69 | 2.6 | 1440 | 8.2 | 72 |

A 200 mg/dL albumin solution (2 g/L=2 mg/mL) was prepared by adding 20.0 mg of Bovine Albumin (Sigma Chemical Co A7906) to 5 mL MAS 1 solution in a 10 mL Volumetric flask, then swirling and allowing to stand until albumin is fully hydrated and then adjusting volume to 10.0 mL with MAS 1.

A 1.0 mg/dL hemoglobin solution (100 mg/mL) was prepared by adding 10 mg of Bovine Hemoglobin lyophilized (Sigma Chemical Co H 2500) to 1 L MAS 1 solution in a 1 L Volumetric flask.

Albumin and hemoglobin detecting reagent areas of 1 $mm^2$ were cut and placed into the microfluidic design shown in FIG. 1 in separate reagent wells and the reaction observed after tested with 2 mg/L albumin or 0.1 mg/dL Hb. The reflectance at 660 nm was measured with digital processing equipment (Panasonic digital 5100 system camera). The reflectance obtained at one minute after adding fluid to the device in urine containing and lacking albumin or hemoglobin was taken to represent strip reactivity.

A 20 μl sample was deposited in well R1 (of the chip design of FIG. 1) and transferred to well R2 and then well R4 by centrifuging at 500 rpm using a 513540 programmable step motor driver from Applied Motion Products, Watsonville, Calif. to overcome the hydrophobic forces in the capillaries connecting R1 to R2 and R2 to R4. The color of the reagent coated filter paper in well R4 was measured before and one Minute after being contacted with 5 μl of the sample. After the analysis the sample liquid was transferred to well R5 by centrifuging at 1,000 rpm.

For each replicate experiment 2 images were taken: one image of the filter before and one image after filing with an incubation time of 1 min. Four replicate experiments were obtained. The reagent paper was also attached to a strip in a manner similar to conventional test strips for comparison.

TABLE B

Results on Hemoglobin Reagent in R4

| Exp. | Sample | Hemoglobin in specimen | Observation |
|---|---|---|---|
| 1 | Hb reagent on strip | 1 mg/dl | Blue |
| 1 | Hb reagent in R4 | 1 mg/dl | Blue |
| 2 | Hb reagent on strip | 0 mg/dl | orange |
| 2 | Hb reagent in R4 | 0 mg/dl | orange |

The hemoglobin reagent in well R4 showed a clear response to hemoglobin in going from blank to 1 mg hemoglobin/dL equal to that of a strip. The reagent filter paper developed a uniform color. The hemoglobin reagents in R4 are soluble and it was found that they can be washed out of chamber R5. The experiment was repeated except that the hemoglobin reagent was placed in well R2 rather than R4.

For each replicate experiment 2 images were taken: one image of the filter before and, one image after filing with an incubation time of 1 min. Four replicate experiments were obtained.

TABLE C

Results on Hemoglobin Reagent in R2

| Exp. | Sample | Hemoglobin in specimen | Observation |
|---|---|---|---|
| 3 | Hb reagent on strip | 1 mg/dl | Blue |
| 3 | Hb reagent in R2 | 1 mg/dl | Blue |
| 4 | Hb reagent on strip | 0 mg/dl | orange |
| 5 | Hb reagent in R2 | 0 mg/dl | orange |

The chip before filing with sample liquid has an orange unreacted pad in well R2 and no color in R3 or R4. After filing with hemoglobin sample, the blue color of the indicator dye for hemoglobin showed in R2. The liquid sample was transported into well R4 by increasing the rotational speed to 1,200 rpm at the end of the experiment.

In a further experiment, the albumin reagent filter paper was placed in well R4 of the design of FIG. 1 and the test repeated.

For each replicate experiment 2 images were taken: one image of the filter before and, one image after filing with an incubation time of 1 min. Four replicate experiments were obtained.

TABLE D

Results on Albumin Reagent in R4

| Exp. | Sample | Hemoglobin in specimen | Observation |
|---|---|---|---|
| 3 | Alb reagent on strip | 1 mg/dl | Blue |
| 3 | Alb reagent in R4 | 1 mg/dl | Blue |
| 4 | Alb reagent on strip | 0 mg/dl | orange |
| 5 | Alb reagent in R4 | 0 mg/dl | orange |

The chip before filling with the sample liquid has the unreacted pad in well R4 and no color in R3 or R2 or R5. After filling with the albumin sample, the blue color of the indicator dye for albumin appeared in R4. The liquid sample was transported into well R5 by increasing the rotational speed to 1,200 rpm at the end of the experiment.

There are various reagent methods which could be substituted for those in the above examples and used in chips of the invention. Reagents undergo changes whereby the intensity of the signal generated is proportional to the concentration of the analyte measured in the clinical specimen. These reagents contain indicator dyes, metals, enzymes, polymers, antibodies and various other chemicals dried onto carriers. Carriers often used are papers, membranes or polymers with various sample uptake and transporting properties. They can be introduced into the reagent wells in the chips of the invention to overcome the problems encountered in analyses using reagent strips.

Reagent strips may use only one reagent area to contain all chemicals needed to generate color response to the analyte. Typical chemical reactions occurring in dry reagent strips can be grouped as dye binding, enzymatic, immunological, nucleotide, oxidation or reductive chemistries. In some cases, up to five competing and timed chemical reactions are occurring within one reagent layer a method for detecting blood in urine, is an example of multiple chemical reactions occurring in a single reagent. The analyte detecting reaction is based on the peroxidase-like activity of hemoglobin that catalyzes the oxidation of a indicator, 3,3',5,5'-tetramethyl-benzidine, by diisopropylbenzene dihydroperoxide. In the same pad, a second reaction occurs to remove ascorbic acid interference, based on the catalytic activity of a ferric-HETDA complex that catalyzes the oxidation of ascorbic acid by diisopropylbenzene dihydroperoxide.

Multiple reagent layers are often used to measure one analyte. Chemical reagent systems are placed into distinct reagent layers and provide for reaction separation steps such as chromatography and filtration. Whole blood glucose strips often use multiple reagents area to trap intact red blood cells that interfere with the color generation layer. Immuno-chromatography strips are constructed with chemical reactions occurring in distinct reagent areas. The detection for human chorionic gonadotropin (hCG) or albumin is an example application of a strip with four reagent areas. The first reagent at the tip of the strip is for sample application and overlaps the next reagent area, providing for transfer of the patent sample (urine) to the first reagent area. The treated sample then migrates across a third reagent, where reactants are immobilized for color development. This migration is driven by a fourth reagent area that takes up the excess specimen. The chromatography reaction takes place in the third reagent area, called the test or capture zone, typically a nitrocellulose membrane. In the first and second layers, an analyte specific antibody reacts with the analyte in the specimen and is chromatographically transferred to the nitrocellulose membrane. The antibody is bound to colored latex particles as a label. If the sample contains the analyte, it reacts with the labeled antibody. In the capture zone, a second antibody is immobilized in a band an captures particles when analyte is present. A colored test line is formed. A second band of reagent is also immobilized in the capture zone to allow a control line to react with particles, forming color. Color at the control line is always formed when the test system is working properly, even in the absence of the hCG in the patient sample. Such multi-step analyses can be transferred to the chips of the invention with the reagent wells being provided with appropriate reagents to carry out the desired analysis.

The albumin analyses described above can also be done by other methods. Proteins such as human serum albumin (HSA), gamma globulin (IgG) and Bence Jones (BJP) proteins can be determined in a variety of ways. The simplest is dye binding where you rely on the color change of the dye as it binds protein. Many dyes have been used: Examples are 2(4-hydroxyphenylazo) benzoic acid [HAPA], bromocresol green, bromocresol blue, bromophenol blue, tetrabromophenol blue, pyrogallol red and bis (3',3"-diiodo-4',4"-dihydroxy-5',5"-dinitrophenyl)-3,4,5,6-tetrabromo sulfonephthalein dye (DIDNTB). Electrophoresis on a variety of substrates has been used to isolate albumin from the other proteins and then staining of the albumin fraction followed by clearing and densitometry. Examples of dyes used here are ponceau red, crystal violet, amido black. For low concentrations of protein, i.e., in the range of <10 mg/L albumin, immunological assays such as immunonephelometry are often used.

Separation steps are possible in which an analyte is reacted with reagent in a first well and then the reacted reagent is directed to a second well for further reaction. In addition a reagent can be re-suspensed in a first well and moved to a second well for a reaction. An analyte or reagent can be trapped in a first or second well and a determination of free versus bound reagent be made.

The determination of a free versus bound reagent is particularly useful for multizone immunoassay and nucleic acid assays. There are various types of multizone immunoassays that could be adapted to this device and would be allowable examples. In the case of adaption of immunochomatography assays, reagents filters are placed into separate wells and do not have to be in physical contact as chromatographic forces are not in play. Immunoassays or DNA assay can be developed for detection of bacteria such as Gram negative species (e.g. *E. Coli, Entereobacter, Pseudomonas, Klebsiella*) and Gram positive species (e.g. *Staphylococcus Aureus, Entereococc*). Immunoassays can be developed for complete panels of proteins and peptides such as albumin, hemoglobin, myoglobulin, α-1-microglobulin, immunoglobulins, enzymes, glyoproteins, protease inhibitors and cytokines. See, for examples: Greenquist in U.S. Pat. No. 4,806,311, Multizone analytical Element Having Labeled Reagent Concentration Zone, Feb. 21, 1989, Liotta in U.S. Pat. No. 4,446,232, Enzyme Immunoassay with Two-Zoned Device Having Bound Antigens, May 1, 1984.

EXAMPLE 2

Demonstration of Re-Suspension of Dried Reagents

Preparation: 5 µl of phenol red solution (0.1% w/w in 0.1 M PBS saline pH 7.0) was dispensed into well R3 of the chip design of FIG. 1 and dried in the vacuum oven at 40° C. for 1 hour. Then, the chip was covered with an adhesive lid before the experiment. A sample of MAS-1 buffer solution was placed in well R1 and transferred into well R3 by centrifuging at 500 rpm as before.

After drying the Phenol red was spread out and covered the whole of well R3. After filling R3 with MAS-1 buffer the phenol red was re-suspended almost instantaneously and could be moved from R3.

10 µl of the phenol red stock solution was dispensed on a 3 mm filter disk (OB filter) and dried in the oven as described above. The filter was placed into R2 after drying then well R1 was filled with MAS-1 buffer and the liquid transferred to well R2.

The chip was not colored before filling with the liquid sample. The Phenol red was spread out and covered the whole well. After filling R3 with MAS-1 buffer the phenol red was re-suspended almost instantaneously and could be completely transferred to well R5.

Potential Applications where dried reagents are resolubilized as in the above example include:

- Filtration
- Sedimentation analysis
- Cell Lysis
- Cell Sorting (mass differences): Centrifugal separation
- Enrichment (concentration) of sample analyte on a solid phase (e.g. microbeads) can be used to improved sensitivity. The enriched microbeads could be separated by continuous centrifugation.
- Multiplexing can be used (e.g. metering of a variety of reagent chambers in parallel and/or in sequence) allowing multiple channels, each producing a defined discrete result. Multiplexing can be done by a capillary array compromising a multiplicity of metering capillary loops, fluidly connected with the entry port, or an array of dosing channels and/or capillary stops connected to each of the metering capillary loops.
- Combination with secondary forces such as magnetic forces can be used in the chip design. Particle such as magnetic beads used as a carrier for reagents or for capturing of sample constituents such as analytes or interfering substances. Separation of particles by physical properties such as density (analog to split fractionation).

EXAMPLE 3

FIG. **4*j* illustrates a chip which can be used to analyze urine. Wells 6 and 8 contain reagents which are used in the analysis, while well 3 is used to receive the sample fluid and well 2 is used to receive a wash liquid. Well 3 is connected to a hydrophilic sample loop L and well 4 is connected to well 2** by a hydrophobic capillary passageway.

Well 6 contains a fibrous pad containing blocking and buffering components, in particular an antibody to the analyte (the component in the sample to be detected), which is attached to a blue-colored latex particle and a different antibody to the analyte which has been labeled with fluorescein. In this example, the analyte is human chorionic gonadotropin (hCG). It reacts with both the antibodies in well 6.

Well 8 contains a nitrocellulose pad to which an antibody to fluorescein has been irreversibly bound. The antibody will react with fluorescein which is transferred into well 8 from well 6.

A sample of urine is added to well 3 and it fills the segment of the hydrophilic capillary passageway between the vents V3 and V4 and stops at hydrophilic stop 5, thus establishing a predetermined amount of the sample which is to be analyzed. Well 2 is filled with a wash liquid, such as a buffered saline solution for removing the blue-colored latex particles which are not bound to the hCG analyte from well 8. The chip is spun at a suitable speed, typically about 500 rpm, causing the defined amount of the sample to flow through stop 5 and into well 6. At the same time the wash liquid flows from well 2 into well 4.

Sufficient incubation time is allowed to pass so that the components in the pad in well 6 are resuspended and both of the antibodies are bound to the analyte in the sample. Then, the chip is spun at a higher rpm (about 1,000 rpm) to transfer the liquid from well 6 to well 8 through the hydrophobic passageway connecting them.

Further incubation time is allowed for the fluorescein labeled analyte antibody to bind to the antibody to fluorescein contained in well 8. The blue-colored latex is thus also attached to the fibrous pad in well 8 since the analyte (hCG) is bound to both antibodies. At this time the blue-color indicating the amount of the analyte is present in well 8, but for improved accuracy, the well is now washed.

The chip is spun a third time at higher rpm (about 2,000 rpm) to transfer the wash liquid from well 4 to well 8 and then to well 9. At the same time all the unbound liquid from well 8 is transferred to well 9. After this step, the color in well 8 can be more easily measured by the camera means used in Example 1. The color is proportional to the concentration of the analyte in the sample, that is, to the amount of the blue-colored latex particles which became bound to the analyte in well 6.

What is claimed is:

1. A microfluidic device for dispensing and analyzing a uniform volume of a liquid sample comprising:

(a) a sample well for receiving and transferring a portion of said liquid sample;

(b) a hydrophilic capillary passageway in liquid communication with said sample well of (a) for receiving a portion of said sample from said sample well of (a), a segment of said hydrophilic capillary passageway disposed between two vents from said hydrophilic capillary passageway to the atmosphere, said segment defining said uniform volume of said liquid sample;

(c) a transfer hydrophilic capillary passageway in liquid communication between said segment of said hydrophilic capillary passageway of (b) and a reagent well, said transfer hydrophilic capillary passageway entering said segment between said two vents to atmosphere, whereby when said uniform volume of said segment is transferred to said reagent well air enters said segment from said two vents and displaces said uniform of liquid sample, (d) a hydrophilic capillary stop disposed within said transfer hydrophilic capillary passageway of (c) between the entrance to said segment and said reagent well, said capillary stop for preventing transfer of said uniform sample volume until the resistance of said capillary stop is overcome by a means for applying force using pressure, vacuum, or electroosmosis.

2. A device of claim 1 further comprising at least one second reagent well in liquid communication through a hydrophilic capillary passageway with said first reagent well.

3. A device of claim 2 further comprising at least one third reagent well in liquid communication through a hydrophilic capillary passageway with at least one of said second reagent wells of claim 2.

4. A device of claim 1 wherein said first reagent well contains a reagent adapted to react with a component contained in said uniform liquid sample.

5. A device of claim 4 wherein said first reagent well contains a reagent adapted to react with a component contained in said uniform liquid sample and thereby produce a response indicating the amount of said component in said liquid sample.

6. A device of claim 4 wherein said first reagent well contains a reagent adapted to react with a component contained in said uniform liquid sample and thereby reduce interference of said component with a second component to be detected.

7. A device of claim 4 wherein said first reagent well contains a reagent adapted to pretreat said liquid sample.

8. A device of claim 5 wherein said first reagent well contains a reagent adapted to react with a component in said liquid sample and thereby produce a reacted component.

9. A device of claim 8 wherein said reacted component is further reacted in a second reagent well to produce a response indicating the amount of said component in said liquid sample.

10. A device of claim 1 wherein the walls of said hydrophilic capillary passageway of (b) have a hydrophilic surface adjusted to provide substantially complete removal of said liquid sample.

11. A device of claim 1 further comprising electrodes disposed in said first reagent well for measuring properties of said sample fluid.

12. A device of claim 2 further comprising electrodes disposed in at least one of said second reagent wells for measuring properties of said sample fluid.

13. A device of claim 3 further comprising electrodes disposed in at least one of said third reagent wells for measuring properties of said sample fluid.

14. A microfluidic device for dispensing and analyzing a uniform volume of a liquid sample comprising:

(a) a sample well for receiving and transferring a portion of said liquid sample;

(b) a hydrophilic capillary passageway in liquid communication with said sample well of (a) for receiving a portion of said sample from said sample well of (a), a segment of said hydrophilic capillary passageway disposed between two vents from said hydrophilic capillary passageway to the atmosphere, said segment defining said uniform volume of said liquid sample;

(c) a transfer hydrophilic capillary passageway in liquid communication between said segment of said hydrophilic capillary passageway of (b) and a reagent well, said transfer hydrophilic capillary passageway entering said segment between said two vents to atmosphere, whereby when said uniform volume of said segment is transferred to said reagent well air enters said segment from said two vents and displaces said uniform of liquid sample, (d) a hydrophobic capillary stop disposed within said transfer hydrophilic capillary passageway of (c) between the entrance to said segment and said reagent well, said capillary stop for preventing transfer of said uniform sample volume until the resistance of said capillary stop is overcome by a means for applying force using pressure, vacuum, or electroosmosis.

15. A device of claim 14 further comprising at least one second reagent well in liquid communication through a hydrophilic capillary passageway with said first reagent well.

16. A device of claim 15 further comprising at least one third reagent well in liquid communication through a hydrophilic capillary passageway with at least one of said second reagent wells of claim 15.

17. A device of claim 14 wherein said first reagent well contains a reagent adapted to react with a component contained in said uniform liquid sample.

18. A device of claim 17 wherein said first reagent well contains a reagent adapted to react with a component contained in said uniform liquid sample and thereby produce a response indicating the amount of said component in said liquid sample.

19. A device of claim 17 wherein said first reagent well contains a reagent adapted to react with a component contained in said uniform liquid sample and thereby reduce interference of said component with a second component to be detected.

20. A device of claim 17 wherein said first reagent well contains a reagent adapted to pretreat said liquid sample.

21. A device of claim 18 wherein said first reagent well contains a reagent adapted to react with a component in said liquid sample and thereby produce a reacted component.

22. A device of claim 21 wherein said reacted component is further reacted in a second reagent well to produce a response indicating the amount of said component in said liquid sample.

23. A device of claim 14 wherein the walls of said hydrophilic capillary passageway of (b) have a hydrophilic surface adjusted to provide substantially complete removal of said liquid sample.

24. A device of claim 14 further comprising electrodes disposed in said first reagent well for measuring properties of said sample fluid.

25. A device of claim 15 further comprising electrodes disposed in at least one of said second reagent wells for measuring properties of said sample fluid.

26. A device of claim 16 further comprising electrodes disposed in at least one of said third reagent wells for measuring properties of said sample fluid.

* * * * *